US008663142B1

(12) United States Patent
Pansiera et al.

(10) Patent No.: US 8,663,142 B1
(45) Date of Patent: Mar. 4, 2014

(54) COMPACT JOINT WITH TWO-AXIS CONSTRUCTION, GEAR REDUCTION, AND RADIAL HYDRAULIC FORCE TRANSFER

(76) Inventors: Timothy Thomas Pansiera, Weaverville, NC (US); David L. Stubbers, Bradenton, FL (US)

(*) Notice: Subject to any disclaimer, the term of this patent is extended or adjusted under 35 U.S.C. 154(b) by 1176 days.

(21) Appl. No.: 12/556,415

(22) Filed: Sep. 9, 2009

Related U.S. Application Data (60) Provisional application No. 61/095,418, filed on Sep. 9, 2008.

(51) Int. Cl.
| | |
|---|---|
| *A61F 5/37* | (2006.01) |
| *A61F 13/00* | (2006.01) |
| *A61B 19/00* | (2006.01) |
| *B62D 11/06* | (2006.01) |
| *F16H 47/04* | (2006.01) |
| *F16H 47/08* | (2006.01) |
| *F16H 57/08* | (2006.01) |
| *A61F 5/00* | (2006.01) |

(52) U.S. Cl.
USPC ............. 602/16; 128/846; 128/869; 128/878; 128/882; 475/22; 475/31; 475/331; 602/5; 602/12; 602/20; 602/23

(58) Field of Classification Search
USPC .......... 602/16, 5, 12, 20, 23; 475/22, 31, 331; 128/846, 869, 878, 882
See application file for complete search history.

(56) References Cited

U.S. PATENT DOCUMENTS

| | | | | |
|---|---|---|---|---|
| 2,671,618 A | * | 3/1954 | Kurlinski ................ 242/530.1 |
| 5,103,811 A | * | 4/1992 | Crupi, Jr. ....................... 602/16 |
| 5,399,149 A | * | 3/1995 | Frankowiak et al. ........... 602/16 |
| 5,472,412 A | * | 12/1995 | Knoth .............................. 602/26 |
| 5,653,680 A | * | 8/1997 | Cruz ................................ 602/21 |
| 5,704,945 A | * | 1/1998 | Wagner et al. .................. 623/44 |
| 6,001,075 A | * | 12/1999 | Clemens et al. ................ 602/16 |
| 6,080,123 A | * | 6/2000 | Pansiera ......................... 602/16 |
| 6,960,175 B1 | * | 11/2005 | Myers ............................. 602/16 |
| 8,317,874 B2 | * | 11/2012 | Pusch et al. .................... 623/46 |
| 2007/0010772 A1 | * | 1/2007 | Ryan .............................. 602/26 |
| 2009/0171469 A1 | * | 7/2009 | Thorsteinsson et al. ........ 623/26 |
| 2010/0191347 A1 | * | 7/2010 | Pusch et al. .................... 623/27 |

OTHER PUBLICATIONS

U.S. Appl. No. 61/083,516, filed Jul. 2008, Pansiera et al.*

* cited by examiner

*Primary Examiner* — Patricia Bianco
*Assistant Examiner* — Brandon L Jackson
(74) *Attorney, Agent, or Firm* — Chambliss, Bahner & Stophel, PC (57) ABSTRACT

A joint having two-axis construction having a distal member and a main member joined in co-linear pivotal relation that provides enhanced joint strength and compactness. Hydraulics further provide variable extension assist and an infinite number of flexion stops for controlled flexion flow, and two gears provide a functional gear ratio that also promotes compact construction by reducing the amount of hydraulic piston travel required for maximum joint extension. A drive gear associated with the main member is positioned between the distal end of the piston and a transfer gear partially press-fit into a cut-out in the distal member, to provide needed radial hydraulic force transfer. Although it is contemplated for joint use to be primarily in orthotic devices that assist the movement of an inadequately functioning body limb, any application for which the mechanical joint's compact configuration would provide assistance or technical advantage is considered to be within its scope.

20 Claims, 4 Drawing Sheets

COMPACT JOINT WITH TWO-AXIS CONSTRUCTION, GEAR REDUCTION, AND RADIAL HYDRAULIC FORCE TRANSFER

CROSS-REFERENCES TO RELATED APPLICATIONS

This patent applications relates to a U.S. provisional patent application filed by the same inventors on Sep. 9, 2008, having a similar title, an application number of 61/095,418. Thus, the applicants herein respectfully request domestic priority based upon this previously filed provisional patent application for the current utility patent application being filed herein.

BACKGROUND

1. Field of the Invention

This invention relates to joints, specifically to a joint using a combination of hydraulics and gears to convert linear hydraulic motion into radial motion and thereby provide both variable extension assist, as well as an infinite number of flexion stops for controlled flexion flow. Applications may include, but are not limited to, joints for orthotic devices which facilitate the extension and flexion of an inadequately functioning human joint, such as a knee. The compact configuration of the present invention would provide the cosmetic advantage of allowing such orthotic devices to fit more easily under clothing wherein they would be less noticeable during use. The present invention joint also has the enhanced strength, enhanced operational efficiency, decreased stress and wear on moving components, and enhanced user comfort and security over the majority of prior art joints used in similar applications. The present invention compact two-axis joint comprises a main member, a distal member, a hydraulic cylinder and piston, a drive gear, and a thickened transfer gear. The distal member has a cut-out area located close to its proximal end and a portion of the thickened transfer gear is press-fit into the cut-out area, leaving the remainder of the transfer gear not press-fit into the cut-out area for interaction with teeth on the drive gear. The opposed end of the distal member is configured for connection to orthotic hardware secured to the lower portion of a body limb. During present invention use for orthotic applications, two independently functioning present invention joints are typically used, one on each side of the inadequately functioning human joint. The hydraulic cylinder, piston, and drive gear are associated with the main member, with the drive gear configured and positioned near its proximal end for providing radial force transfer between the hydraulic piston and the transfer gear. The main member further has an end opposed from the drive gear that is configured for connection to orthotic hardware secured to the upper portion of a body limb. When the present invention joint is in its fully extended orientation, the distal member extends from the main member in a direction substantially opposite to that of the main member. Furthermore, movement of the distal member relative to the main member between positions of complete flexion and full extension is approximately the full 135-degree range of anatomical motion, resulting in an approximate 45-degree angle between the distal member and the main member when the distal member is in a position of complete flexion relative to the main member. The present invention's hydraulic piston, in combination with the drive gear and transfer gear that provide a functional gear ratio (often a 2:1 gear ratio in orthotic applications), allows the use of a smaller hydraulic cylinder (and less piston travel). A spring biasing member is located in a remote control valve assembly, allowing the use of a much larger spring while being less noticeable. Furthermore, a two axis (co-linear) construction that further enhances joint strength and compactness is used for the pivotal connection between the distal member and the main member.

2. Description of the Related Art

Particularly in the field of orthotic devices relating to the support of a human knee, there is a need for a joint which can assist in the forward movement of a person's lower leg and foot, and which will also exhibit a controlled flexion moment at the knee once the person's foot is planted on a floor or ground surface and his or her weight is shifted forward over the joint. For social acceptability, it is also desirable to have orthotic devices which are minimally obtrusive. Many joints are known which comprise varying combinations of springs, gears, levers, and cables and which can hold a joint in a limited number of angles of flexion and provide a limited amount of extension assist. However, none provides all of the advantages of the present invention that derive from the combined use of hydraulic forces, two gears providing a gear ratio, and a two-axis (co-linear) construction. It is not known to have a cosmetically advantageous and compactly designed joint which provides adjustable extension assist, as well as an infinite number of flexion stops to prevent sudden collapse of the joint under a shifting weight load, through the combined use of hydraulic forces and gears that radially transfer the linear hydraulic forces applied. In addition in orthotic applications, components used should be compact and minimally intrusive for ease of use, enhanced social acceptability, and a lessened risk of hazard or damage during use. Further, a user should not experience insecurity, discomfort, or apprehension as a result of any aspect of orthotic device performance. As a fundamental part of their construction, all joints used in orthotic devices must include design features and/or apparatus that define the limits of their flexion and extension, and movement provided therebetween should avoid excesses and insufficiencies of motion. Often, mechanical joints are bulky in configuration, provide an abrupt stop for the user, and/or fail to provide proper support for a user when the joint nears maximum extension. Orthotic devices should also be as simple as possible for ease of manufacture and convenience during their function. The use of a hydraulic piston in combination with two gears provide improved interior design that is new in the field of orthotic joints, and produce a functional gear ratio (preferably 2:1 or close thereto in many applications) that allows less hydraulic piston travel. Furthermore, the distal member and the main member are pivotally connected to one another using a two-axis (co-linear) construction that provides further compactness and operational efficiency in the present invention joint. No other joint is known to have the same structure, function in the same manner, or provide all of the advantages of the present invention.

BRIEF SUMMARY OF THE INVENTION

It is the primary object of this invention to provide a joint which has variable extension assist in combination with an infinite number of flexion stops for controlled flexion flow. It is also an object of this invention to provide a joint which achieves variable extension assist and controlled flexion flow through the introduction of linear hydraulic forces against a drive gear that interacts with a transfer gear to provide a functional gear ratio. A further object of this invention is to provide a joint which has sufficient strength for use in orthotic devices such as those employed to support a human knee. It is also an object of this invention to provide a compactly configured joint which can help orthotic devices fit more easily under clothing wherein they would function unobtrusively and be less noticeable during use. A further object of this invention is to provide a joint made from durable materials in which the amount of extension assist and flexion flow is either automatically controlled, or easily and readily controlled by the user. Another object of this invention to provide a joint for an orthotic device that has pediatric applications. It is a further object of this invention is to provide a joint for an orthotic device that is simple and cost-effective to assemble and manufacture.

As described herein, properly manufactured and connected to cooperating members of a device requiring a joint having at least minimal amounts of extension assist and controlled flexion flow, the present invention would provide a joint which uses hydraulic force in combination with two gears providing a functional gear ratio to convert applied linear motion into radial motion. Manual control by the user of the amount of hydraulic force introduced into a hydraulically sealed cylinder provides differing amounts of extension assist according to user preference or need, in addition to an infinite number of flexion stops. Automated control of hydraulic flow is also contemplated. In the preferred embodiment of the present invention, the stationary main member is connected to the upper portion of an inadequately functioning limb and comprises a hydraulically sealed cylinder with a piston having a first end within the cylinder and a second end in contact with a protrusion on a drive gear also associated with the main member. Although not shown, during use of the present invention the male hydraulic fitting associated with the fluid-tight hydraulic cylinder is in communication with a hydraulic reservoir (not shown) via a fluid supply line (not shown) to provide variable joint extension assist, while a one-way valve and an easily-manipulated valve control can be employed by a user to adjust the fluid pressure and volume within the fluid-tight hydraulic cylinder and would determine the resulting flexion or extension response of the present invention joint, which could range from that of full lock to free action with varying levels of pressure return. Further, although the present invention is particularly effective in pediatric orthotic applications, other orthotic applications are also important to the present invention, and it is further contemplated for use in any other application where substantially similar design features in a mechanical joint are required or beneficial. The present invention joint has improved interior design, which uses a transfer gear with an enlarged thickness dimension in combination with the drive gear to provide a functional gear ratio. A portion of the transfer gear becomes press-fit into a cut-out area located close to the proximal end of the distal member, which in orthotic applications is connected to the lower portion of an inadequately functioning limb. Movement of distal member relative to main member between positions of complete flexion and full extension is approximately the full 135-degree range of anatomical motion, and when the present invention joint is in its fully extended orientation, the main member extends from the joint in a direction substantially opposite to that of the distal member. The adjacent portion of the transfer gear not becoming press-fit into the distal member is in contact with the teeth of the drive gear, which also has a protrusion in a position substantially opposed to its teeth. It is this protrusion that is placed into contact with the distal end of the hydraulic piston exposed through the end of the hydraulic cylinder opposed from the male hydraulic fitting. Thus, although it is contemplated for the transfer gear to have teeth evenly spaced about its perimeter, the drive gear in the present invention has teeth only on one of its sides. As a result, when hydraulic fluid from a reservoir (not shown) moves the piston toward the present invention drive gear, the distal end of the piston in contact with the protrusion on the drive gear pushes against the protrusion and causes the drive gear to rotate in a counterclockwise direction. The counterclockwise rotation of the drive gear forces the transfer gear to move in a clockwise direction, which causes movement of the distal member away from the main member and toward a position of full extension. The differing configuration of the transfer gear, as compared to the drive gear, produces a functional gear ratio (preferably 2:1 in many orthotic applications), which allows the use of a smaller hydraulic cylinder than has been possible in prior art orthotic devices (resulting in as less travel of the piston for a more compact joint configuration), less stress and wear on gear teeth, and enhanced joint strength. The transfer gear press-fit connection also simplifies construction and results in a more compact mechanical joint that provides cosmetic advantage in orthotic applications. Together with the present invention two-axis pivotal construction, the functional gear ratio and press-fit transfer gear synergistically provide an even more compact construction for an assembled joint to permit it to function less obtrusively. The above-mentioned structure and other design features of the present invention make it compact, strong, efficient, and comfort-enhancing for its user. In addition, the compact design of the present invention which results from the radial hydraulic force transfer would promote social acceptability of the orthotic devices to which it was attached by giving them the cosmetic advantage of being able to fit more easily under clothing wherein they would be less obtrusive during use. No other mechanical joint for orthotic use is known to have the same structure, function in the same manner, or provide all of the advantages of the present invention.

While the description herein provides preferred embodiments of the present invention as it would be used in support of a human knee, such preferred embodiments should not be construed as limiting the scope of the present invention. For example, it is within the contemplation of the present invention to incorporate variations other than those shown and described herein, such as variations in the diameter dimension of the stop pin used; the number of gear teeth used in the transfer gear and the drive gear as long as a needed functional gear ratio is achieved; the means used for securing the pivot points in the main member and the distal member; the diameter dimensions of pivot screws (when they are used); the perimeter configuration of the cover; the size, type, number, and location of fasteners used to attach the cover to the main member; the dimension, configuration, and positioning of the bar receivers in the attachment ends of both the distal member and the main member; whether control of distal member movement is automated or manual; and the materials from which the main member and distal members are made. Thus, the scope of the present invention should be determined by the appended claims and their legal equivalents, rather than being limited to the examples given.

BRIEF DESCRIPTION OF THE SEVERAL VIEWS OF THE DRAWINGS

FIG. 1 is a sectional view of the most preferred embodiment of the present invention in a position allowing complete or near complete extremity flexion and showing the piston nearly filling the hydraulic cylinder surrounding it, with FIG. 1 further showing the distal end of the piston engaging the protrusion on the drive gear associated with the main member while the stop pin shown is not in contact with any teeth on the larger diameter drive gear, in addition with FIG. 1 showing a thickened transfer gear partially press-fit into a cutout in the proximal end of a rotationally movable distal member, and the portion of the thickened transfer gear no press-fit becoming engaged with the teeth of the drive gear (although such engagement is hidden from view in FIG. 1), and a right-directed arrow further showing the direction of hydraulic fluid movement needed to attain the flexion positioning shown, as well as the letters "A" and "B" being used to designate the co-linear axis construction of the present invention mechanical joint.

FIG. 2 is a sectional view of the most preferred embodiment of the present invention in a position of maximum or near maximum extension where the distal member extends in an opposing direction from the main member, with the piston shown moved partially from the associated hydraulic cylinder and the protrusion of the drive gear shown moved in a counterclockwise direction by the distal end of the piston until the advancing teeth on the opposed portion of the drive gear engage a stop pin that blocks further travel of the distal member away from the main member, and further with two left-directed arrows in a row showing the direction of hydraulic fluid movement needed to attain the positioning shown, as well as the letters "A" and "B" designating the co-linear axis construction of the present invention mechanical joint.

COMPONENT LIST IDENTIFYING REFERENCE NUMBERS USED IN THE DRAWINGS

1—main member bar receiver (configured to secure main member 14 to a bar 17 attached to orthotic hardware used with the upper portion of a body limb)
2—hydraulic connector/line (used for introduction of hydraulic fluid into the hydraulic cylinder in the main member 14 to provide movement of the distal member 6 toward a position of full extension and removal of hydraulic fluid from the hydraulic cylinder 9 to cause opposing movement of the distal member 6 toward a position of full flexion)
3—hydraulic piston (its distal end 15 engages the protrusion 13 of the drive gear 4)
4—drive gear (associated with the main member 14 and together with thickened transfer gear 5 it provides the preferred advantageous gear ratio reduction of approximately 2:1 for increased dynamic range of motion, with a protrusion 13 that operatively engages the distal end 15 of the hydraulic piston 3)
5—thickened transfer gear (one of the two gears providing a functional gear ratio in the present invention, preferably 2:1 in many contemplated applications, but not limited thereto, that provides the advantage of reducing the stop increment during extension movement of distal member 6 for better simulation of natural body motion particularly for children and others with shorter legs, and also providing a more compact joint for less conspicuous presence and enhanced user comfort, reduced travel of distal member 6 between stops that provides reduced stress on gear teeth 12, and enhanced joint strength, with transfer gear 5 having a thickened dimension, one portion of which is positioned to sequentially engage the teeth of drive gear 4 while a second adjacent portion of the thickened transfer gear 5 is press-fit into a cut-out area 22 near to the proximal end of distal member 6 that is similar in configuration to the perimeter surface of transfer gear 5 and collectively includes the shape of all gear teeth present on transfer gear 5, with the press-fit connection allowing distal member 6 and transfer gear 5 to rotate together).
6—distal member (its proximal end has a cut-out area 22 similar in configuration to the perimeter surface of transfer gear 5 and collectively includes the shape of all the teeth of transfer gear 5, and its opposing end has a bar receiver 7 configured to secure distal member 6 to a bar attached to orthotic hardware, such as but not limited to bar 18 in FIG. 3)
7—distal member bar receiver (configured in orthotic applications to secure distal member 6 to a bar 18 attached to orthotic hardware used with the lower portion of a body limb)
8—stop pin (is secured to main member 14 to limit rotation of distal member 6 and block the movement of distal member 6 beyond a position of maximum extension as it is moved away from main member 14 and toward a position of full extension)
9—hydraulic cylinder (houses hydraulic piston 3)
10—fastener holes in main member 14 for attachment of cover 16
11—fastener holes in bar receivers 1 and 7 for attachment of orthotic hardware
12—teeth on drive gear 4 (which engage the teeth on transfer gear 5)
13—protrusion on the drive gear 4 (engages the distal end 15 of piston 3 and is in an opposed location on drive gear 4 from its teeth 12)
14—main member
15—distal end of piston 3 (engages the protrusion on the drive gear 4)
16—gear-protecting cover (secured to main member 14 via fastener holes 10 and fasteners 20, and provides protection for all moving internal parts in the present invention joint from damaging contact, as well as malfunction resulting from the presence of dirt and debris)
17—bar of a first orthotic member used for attachment to the upper portion of a body limb
18—bar of a second orthotic member used for attachment to the lower portion of a body limb
19—fastener used for attachment of bar receivers 1 and 7 to orthotic hardware
20—fastener used for attachment of gear-protecting cover 16 to main member 14
21—pivot screw (secures distal member 6 in pivoting relation to main body 14)

22—cut-out area in distal member 6 (it is similar in configuration to the perimeter surface of transfer gear 5 and collectively includes the shape of all the teeth of transfer gear 5)

A—axis of rotation for the drive gear 4 (it is co-linear with the axis of rotation B for distal member 6 and transfer gear 5)

B—axis of rotation jointly for the transfer gear 5 and the distal member 6 (it is co-linear with the axis of rotation A for the drive gear 4)

DETAILED DESCRIPTION OF THE INVENTION

The present invention provides a mechanical joint that better simulates natural body motion through use of variable extension assist for its distal member 6, as well as an infinite number of flexion stops for controlled flexion flow, making it particularly effective in pediatric orthotic applications to assist in the movement of an inadequately functioning body limb (not shown). However, the present invention is also effective for other orthotic applications, as well as use in any device needing a mechanical joint for which the compact configuration and/or strength of the present invention would provide some assistance or technical advantage. Another benefit of the present invention although not limited thereto, is an increase in dynamic range of motion. It comprises a transfer gear 5 with an enlarged thickness dimension and a distal member 6 with a cut-out area 22 located close to its proximal end that has a shape complementary to the portion of the transfer gear 5 perimeter collectively defined by its teeth. A portion of the thickened transfer gear 5 is press-fit into cut-out area 22, with an opposed end of distal member 6 configured as a bar receiver 7 for connection to a bar 18 that is attached to orthotic hardware (not shown) secured to the lower portion of a body limb (not shown). The present invention mechanical joint also comprises a main member 14 associated with a hydraulic piston 3 and cylinder 9, with main member 14 also having a proximal end associated with a drive gear 4 that is operative between the hydraulic piston 3 and the transfer gear 5 to provide a functional gear ratio, with main member 14 further having an opposed end that is configured as a bar receiver 1 for connection to a bar 17 that is attached to orthotic hardware secured to the upper portion of a body limb. Movement of distal member 6 relative to main member 14 between positions of complete flexion and full extension is approximately the full 135-degree range of anatomical motion. Therefore, instead of using a spring biasing member, as in many prior orthotic joints, the hydraulic piston 3 of the present invention, in combination with the two gears (drive gear 4 and thickened transfer gear 5) providing a functional gear ratio (preferably 2:1 in many orthotic applications), allows an infinite number of flexion positions for distal member 6. When the present invention mechanical joint is in its fully extended orientation, distal member 6 extends from main member 14 in a direction substantially opposite to that of main member 14. Furthermore, a space-saving two axis (co-linear) construction (see A, B in FIGS. 1-3) that further enhances joint strength and compactness is used for pivotal connection of distal member 6 and main member 14. Thus, when hydraulic fluid is introduced into cylinder 9 (as in FIG. 2), piston 3 is moved toward drive gear 4 until its distal end 15 engages the protrusion 13 on drive gear 4 and moves drive gear 4 in a counterclockwise direction around axis A. Automated and manual control of a valve allowing hydraulic fluid to enter cylinder 9 are both contemplated. Since the teeth 12 of drive gear 4 engage teeth on transfer gear 5, as teeth 12 of drive gear 4 are moved by piston 3 in a counterclockwise direction, transfer gear 5 is forced to move in a clockwise direction that causes distal member 6 to move away from main member 14. When teeth 12 of drive gear 4 eventually reach and engage stop pin 8, the position of full extension for distal member 6 is achieved, with stop pin 8 blocking further rotation of distal member 6. In contrast, as shown in FIG. 2, to move distal member 6 toward main member 14 and achieve a position of maximum flexion, gears 4 and 5 in combination force piston 3 back into cylinder 9, and hydraulic fluid to flow from cylinder 9 through hydraulic connector/line 2 and into a reservoir (not shown).

Figure 1:
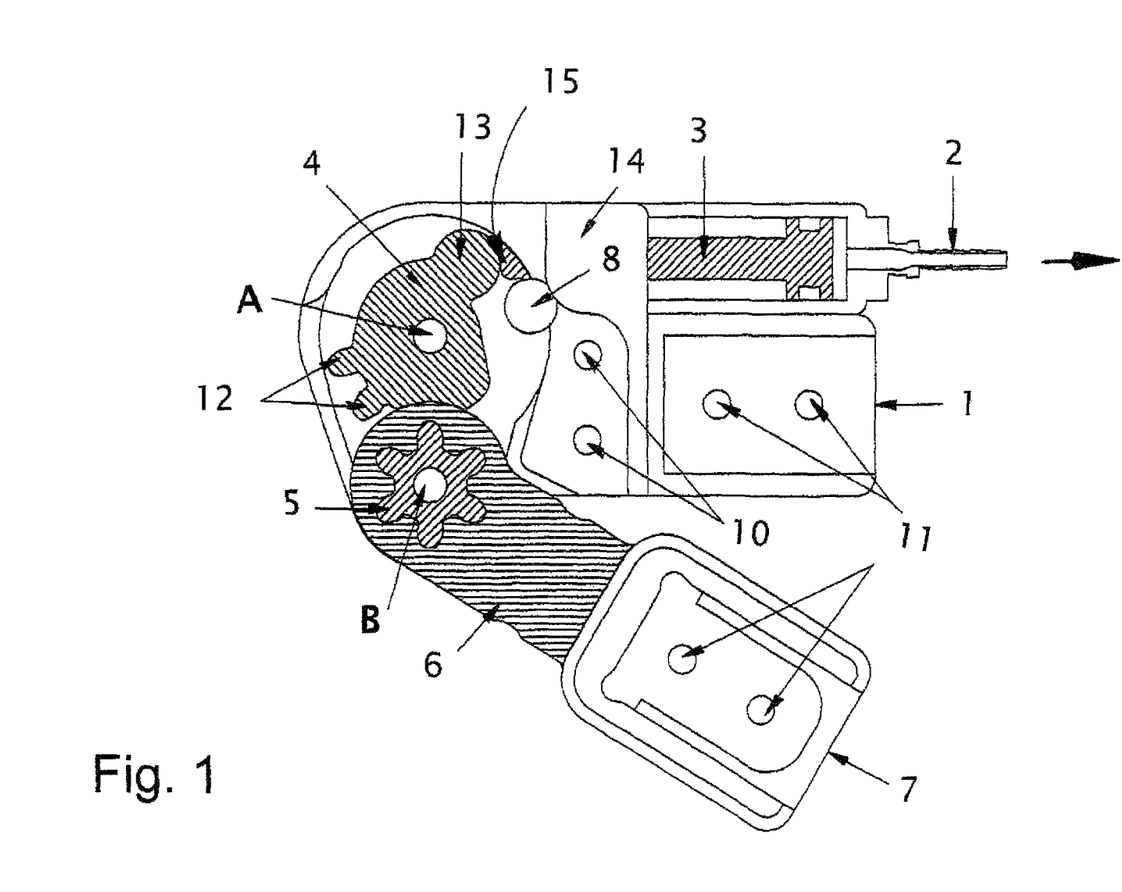
Figure 2:
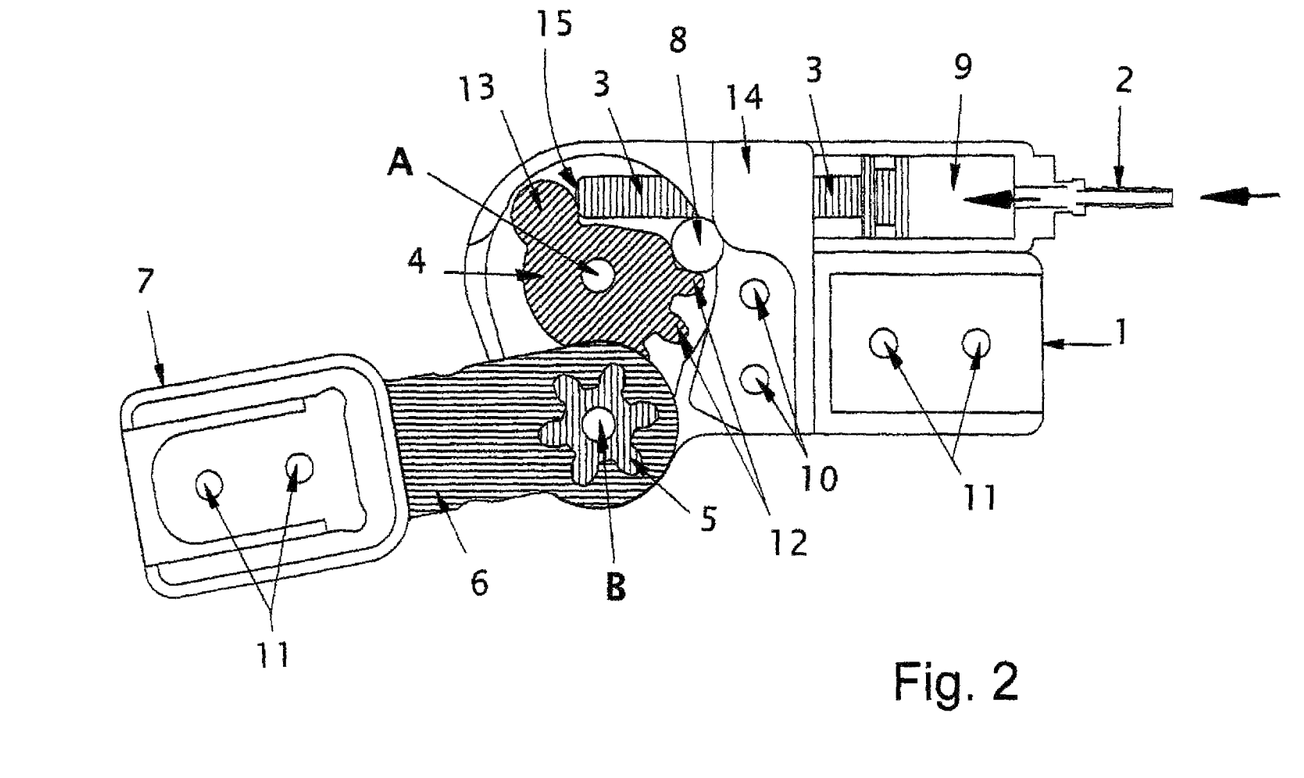
Figure 3:
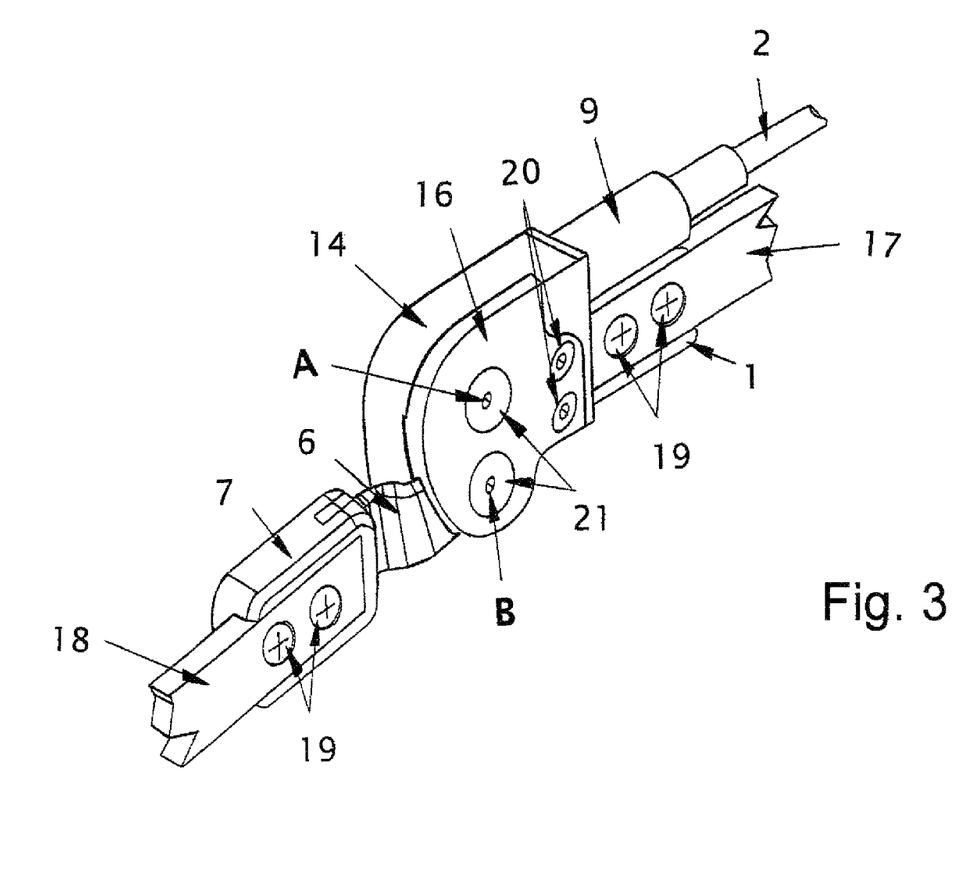
FIG. 3 is an isometric view of the most preferred embodiment of the present invention mechanical joint with an outer cover (hereinafter also referred to as main cover) held securely in place to the joint's main body with pivot screws, wherein the main cover in the preferred position of use shown provides joint stability and also protects the transfer gear, the drive gear and the distal end of the piston from damaging contact, as well as interference from dirt and debris, with FIG. 3 also showing bar receivers 1 and 7 attached to bars connected on their hidden opposing ends to orthotic hardware.

FIGS. 1 and 2 show the most preferred embodiment present invention mechanical joint during its use for assisted movement of an inadequately functioning body limb (not shown). FIG. 1 is a sectional view of the most preferred embodiment of the present invention in a position allowing complete or near complete extremity flexion. FIG. 1 shows piston 3 nearly filling the hydraulic cylinder 9 surrounding it (the number 9 for the cylinder is marked in FIG. 2), with FIG. 1 further showing the distal end 15 of piston 3 engaging the protrusion 13 on the drive gear 4 associated with main member 14. While in a position of complete or near complete extremity flexion, the stop pin 8 shown in FIG. 1 is not in contact with any teeth 12 on drive gear 4. FIG. 1 also shows a hydraulic connector/line 2, right-directed arrow positioned to the right of hydraulic connector/line 2 that indicates the direction of hydraulic fluid (not shown) movement needed to attain the flexion positioning shown. In addition, FIG. 1 includes the letters "A" and "B" that are used to designate the co-linear axis construction of the present invention mechanical joint. In FIG. 1, as well as in FIGS. 2 and 3, the axis of rotation associated with main member 14 is identified by the letter "A" and shown in a co-linear arrangement with the axis of rotation for the distal member 6 that is identified by the letter "B". In contrast, FIG. 2 is a sectional view of the most preferred embodiment of the present invention in a position of maximum or near maximum extension where the distal member 6 extends in an opposing direction from main member 14. Also in FIG. 2, the distal end 15 of piston 3 is shown moved further away from hydraulic cylinder 9 and the protrusion 13 of the drive gear 4 is shown moved in a counterclockwise direction (from the position shown in FIG. 1) as a result of contact with the moving distal end 15 of piston 3. Movement of drive gear 4 can continue until the teeth 12 on the portion of the drive gear 4 opposed from protrusion 13 reach and make contact with a stop pin 8 that blocks further rotation of drive gear 4, and correspondingly blocks further travel of distal member 6 away from main member 14. Although the preferred interior placement of stop pin 8 within main body 14 is shown in FIGS. 1 and 2, it is not contemplated for the size and placement of stop pin 8 shown in FIGS. 1 and 2 to be critical for all applications of the present invention. Similar to FIG. 1, FIG. 2 also shows the letters "A" and "B" designating the co-linear axis construction of the present invention mechanical joint. However, in contrast to FIG. 1, FIG. 2 shows two arrows adjacent to hydraulic connector/line 2 and hydraulic cylinder 9 in a row that identify the direction of hydraulic fluid (not shown) movement needed to attain the positioning shown. FIGS. 1 and 2 also both show the fastener holes 10 in main member 14 that are used to connect the gear-protecting cover 16 to main member 14 via fasteners 20, so as to provide protection for all moving internal parts in the present invention mechanical joint from damaging contact, as well as malfunction resulting from the presence of dirt and debris. FIGS. 1 and 2 further both show the fastener holes 11 in bar receivers 1 and 7 that are used respectively to attach one end of bars 17 and 18, each of which are secured on an opposing end to orthotic hardware (not shown). The number of fastener holes 10 and 11 used can vary from that shown in FIGS. 1 and 2. However, the number used in the present invention should be appropriate to the needed application, so as to provide optimum benefit with minimal increase in manufacturing cost. As shown in FIG. 3, fasteners 19 are used to maintain the connection of bars 17 and 18 respectively to bar receivers 1 and 7. Materials for all components shown in FIGS. 1 and 2 should have enhanced strength, enhanced resistance to wear, efficient operation in a wide range of ambient temperatures, and the capability of withstanding repeated exposure to humid environments without premature deterioration. Furthermore, although the components shown in FIGS. 1 and 2 represent the most preferred embodiment of the present invention, some variation thereof is contemplated and considered to also be within the scope of the present invention. Therefore, one should consult the appended claims for a determination of the full scope of the present invention.

FIG. 3 is an isometric view of the most preferred embodiment of the present invention mechanical joint with an outer cover 16 that is held securely in place to the joint's main body 14 with pivot screws 21 and fasteners 20. In its preferred position of use shown in FIG. 3, outer cover 16 provides joint stability and also protects the thickened transfer gear 5, the drive gear 4, and the distal end 15 of piston 3 from damaging contact, as well as interference from dirt and debris (not shown). Another difference between FIG. 3 and FIGS. 1 and 2, is that FIG. 3 also shows bar receivers 1 and 7 each respectively attached to one end of bars 17 and 18, which have an opposing end (hidden from view in FIG. 3) that is connected orthotic hardware (not shown). The reservoir that provides the hydraulic fluid for cylinder 9 is also not shown, but can be similar in configuration to prior art reservoirs, although it would be smaller since less travel of piston 3 is required for movement of distal member 6 through the full 135-degree range of anatomical motion. Although not shown or marked with a numerical designation, each pivot screw 21 and fastener 20 may have a central hex indentation that facilitates prompt and secure tightening, as well as its prompt removal when needed. The use of a hex indentation on pivot screws 21 and fasteners 20 used to secure outer cover 16 is merely provided as an example, and any geometric or other non-slip configuration can also be alternatively used.

Figures 4, 5:
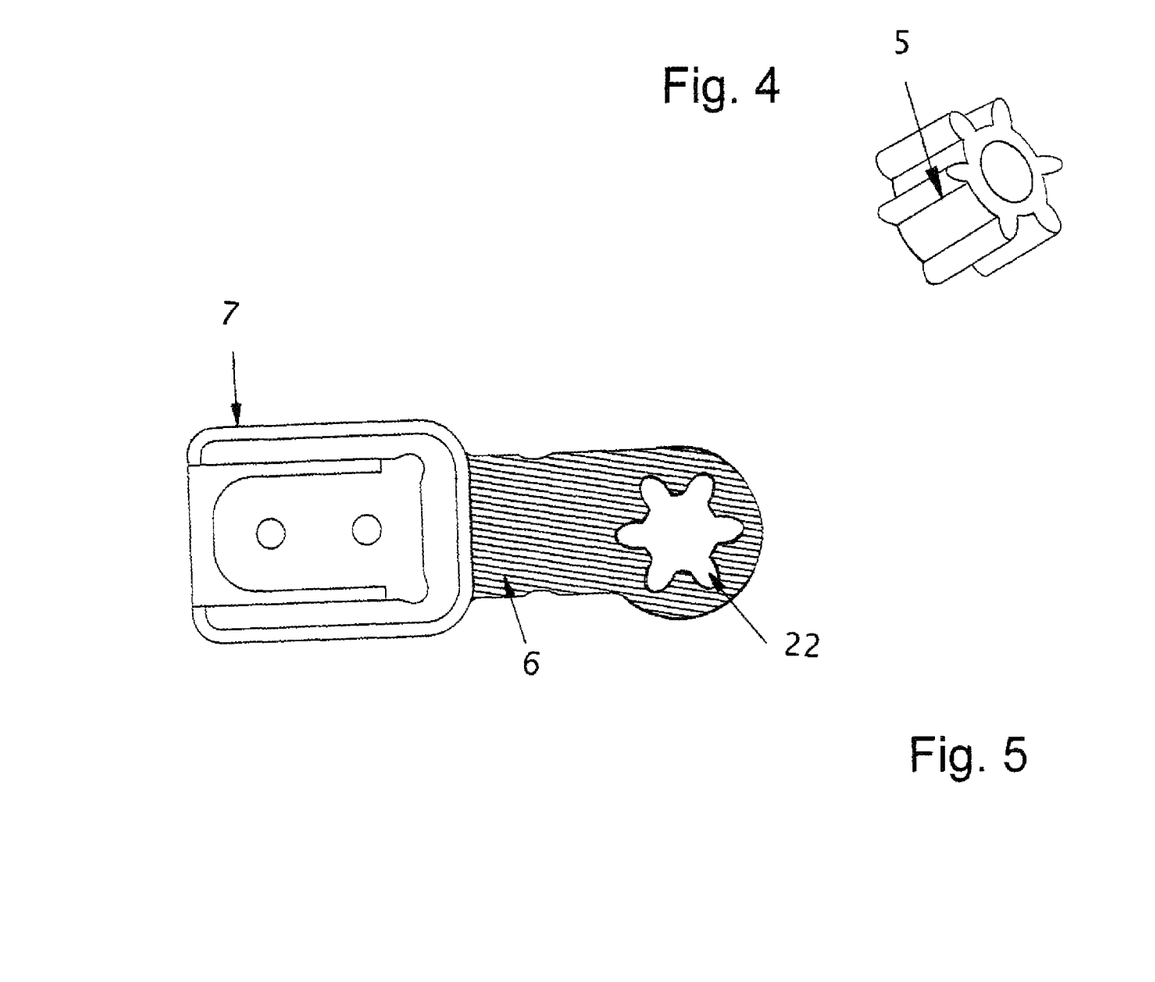
FIG. 4 is an isometric view of a preferred embodiment of transfer gear that can be used as a part of the most preferred embodiment of the present invention mechanical joint and showing its thickened configuration.
FIG. 5 is a side view of the distal member in the most preferred embodiment of the present invention mechanical joint which shows the cut-out area used for press-fitting a portion of the transfer gear to provide a firm connection between the transfer gear and the distal member during movement of the distal member toward and away from the main member.

FIGS. 4 and 5 show more detailed views of the thickened transfer gear 5 and the cut-out area 22 in the proximal end of distal member 6 that is used for a press-fit connection of a portion of the thickened transfer gear 5. FIG. 4 is an isometric view of a preferred embodiment of a thickened transfer gear 5 that can be used as a part of preferred embodiments of the present invention. Its thickened configuration is more clearly shown than in FIGS. 1-3. In contrast, FIG. 5 is a side view of the distal member 6 that is a part of the most preferred embodiment of the present invention, and it shows the cut-out area 22 used to press-fit a portion of the thickened transfer gear 5 to provide a firm connection between transfer gear 5 and distal member 6 during movement of distal member 6 toward and away from main member 14. The size, configuration, and number of teeth on thickened transfer gear 5 may be different from that shown in FIGS. 4 and 5, as long as the needed functional gear ratio with drive gear 4 is maintained.

We claim:

1. A compact joint having two-axis construction that uses a combination of hydraulics and gears to convert linear hydraulic motion into radial motion and thereby provide variable extension assist and an infinite number of flexion stops for controlled flexion flow, said joint having:
    a distal member having a proximal end, and a cut-out area therethrough close to said proximal end;
    a main member joined in co-linear pivotal relation to said distal member;
    a hydraulic cylinder and piston configured and positioned to provide variable extension assist and an infinite number of flexion stops for controlled flexion flow during movement of said distal member relative to said main member, said hydraulic piston having a distal end;
    a drive gear associated with said main member and having a protrusion positioned in contact with said distal end of said piston, said drive gear also having a plurality of gear teeth; and
    a thickened transfer gear having a plurality of gear teeth forming a perimeter configuration for said transfer gear that is similar to that of said cut-out area in said distal member, said perimeter configuration being slightly smaller in dimension than said cut-out area, and said perimeter configuration also being partially press-fit into said cut-out area, with said gear teeth of said drive gear and said gear teeth of said transfer gear in contact with one another and providing a functional gear ratio that also promotes compact joint construction by reducing the amount of travel required by said piston to achieve maximum extension of said distal member relative to said main member, wherein when hydraulic pressure is increased within said hydraulic cylinder, linear motion of said piston toward said protrusion of said drive gear rotates said drive gear providing radial hydraulic force transfer and variable extension assist for movement of said distal member relative to said main member, and rotation of said drive gear causes rotation of said transfer gear and movement of said distal member relative to said main member toward a position of maximum extension, with adjustment of hydraulic pressure in said hydraulic cylinder also determining flexion response of said distal member relative to said main member, which is able to range from full lock to free action with varying levels of pressure return, providing an infinite number of flexion stops for controlled flexion flow in the movement of said distal member relative to said main member toward a position of maximum flexion.

2. The joint of claim 1 further comprising a stop pin associated with said main member that is positioned to define a position of maximum extension for said distal member.

3. The joint of claim 2 wherein said protrusion is located in a position adjacent to said pin stop when said distal member is in said position of maximum flexion and further located in a position remote from said pin stop when said distal member is in said position of maximum extension.

4. The joint of claim 1 further comprising movement of said distal member relative to said main member between said positions of maximum flexion and maximum extension that is approximately the full 135-degree range of anatomical motion.

5. The joint of claim 4 wherein when said distal member is in said position of maximum flexion relative to said main member, an approximate 45-degree angle exists between said distal member and said main member.

6. The joint of claim 1 further comprising a cover configured and positioned against said main member in a protective position over said drive gear and said transfer gear.

7. The joint of claim 6 further comprising two pivot screws configured and positioned to establish said co-linear pivotal relation between said main member and said distal member, and wherein said pivot screws are also configured for retaining said cover in said protective position.

8. The joint of claim 6 wherein said main member further comprises at least one fastener hole configured for use in connecting said cover to main member.

9. The joint of claim 1 wherein said gear teeth of said transfer gear are evenly spaced apart around said perimeter configuration of said transfer gear.

10. The joint of claim 9 wherein said drive gear has a perimeter dimension and said gear teeth of said drive gear extend across less than half of said perimeter dimension.

11. The joint of claim 1 further comprising a stop pin associated with said drive gear that is positioned to define a position of maximum extension for said distal member, wherein said protrusion is located in a position adjacent to said pin stop when said distal member is in said position of maximum flexion and further located in a position remote from said pin stop when said distal member is in said position of maximum extension, wherein said joint further comprises two pivot screws configured and positioned to establish said co-linear pivotal relation between said main member and said distal member, said joint further comprising a cover configured and positioned against said main member in a protective position over said drive gear and said transfer gear, wherein said two pivot screws are also configured for use in retaining said cover in said protective position, wherein said distal member further comprises a first bar receiver configured for attachment to a bar connected to orthotic hardware adapted for use with the lower portion of a body limb, and also wherein said main member further comprises a second bar receiver configured for attachment to a bar connected to orthotic hardware adapted for use with the upper portion of the same body limb.

12. The joint of claim 11 wherein forward movement of said distal end of said hydraulic piston against said protrusion on said drive gear causes said drive gear to rotate in a counterclockwise direction, which further forces said transfer gear to move in a clockwise direction and movement of said distal member away from said main member, toward a position of maximum extension.

13. The joint of claim 12 further comprising movement of said distal member relative to said main member between said positions of maximum flexion and maximum extension that is approximately the full 135-degree range of anatomical motion, and further wherein when said distal member is in said position of maximum flexion relative to said main member, an approximate 45-degree angle exists between said distal member and said main member.

14. The joint of claim 13 wherein control of hydraulic pressure in said hydraulic cylinder is selected from a group consisting of automated control and manual control.

15. The joint of claim 1 further comprising two pivot screws configured and positioned relative to said main member and said distal member to establish said co-linear pivotal relation between said main member and said distal member.

16. The joint of claim 1 wherein control of hydraulic pressure in said hydraulic cylinder is selected from a group consisting of automated control and manual control.

17. The joint of claim 1 wherein said drive gear has a perimeter dimension and said gear teeth of said drive gear extend across less than half of said perimeter dimension.

18. The joint of claim 1 wherein forward movement of said distal end of said hydraulic piston against said protrusion on said drive gear causes said drive gear to rotate in a counterclockwise direction, which further forces said transfer gear to move in a clockwise direction and movement of said distal member away from said main member, toward a position of maximum extension.

19. The joint of claim 1 wherein said distal member further comprises a first bar receiver configured for attachment to a bar connected to orthotic hardware adapted for use with the lower portion of a body limb and said main member further comprises a second bar receiver configured for attachment to a bar connected to orthotic hardware adapted for use with the upper portion of the same body limb.

20. The joint of claim 1 wherein materials for said main member, said distal member, said drive gear, and said transfer gear are selected from a group consisting of materials having enhanced strength, materials having enhanced resistance to wear, materials having efficient operation in a wide range of ambient temperatures, and materials having a capability for withstanding repeated exposure to humid environments without corrosion and premature deterioration.

* * * * *